(12) United States Patent
Yu (10) Patent No.: US 10,820,952 B2
(45) Date of Patent: Nov. 3, 2020

(54) ROTATIONAL SUPPORT FOR AN ELONGATE MEMBER

(71) Applicant: Auris Health, Inc., Redwood City, CA (US)

(72) Inventor: Alan Yu, Union City, CA (US)

(73) Assignee: Auris Heath, Inc., Redwood City, CA (US)

( * ) Notice: Subject to any disclaimer, the term of this patent is extended or adjusted under 35 U.S.C. 154(b) by 507 days.

(21) Appl. No.: 15/270,592

(22) Filed: Sep. 20, 2016

(65) Prior Publication Data

US 2017/0007343 A1    Jan. 12, 2017

Related U.S. Application Data

(63) Continuation of application No. 13/833,531, filed on Mar. 15, 2013, now Pat. No. 9,452,018.

(51) Int. Cl.
*A61B 34/37* (2016.01)
*A61M 25/09* (2006.01)
*A61B 34/30* (2016.01)

(52) U.S. Cl.
CPC .............. *A61B 34/37* (2016.02); *A61B 34/30* (2016.02); *A61M 25/09041* (2013.01); *A61B 2034/301* (2016.02)

(58) Field of Classification Search
CPC ......... A61B 34/37; A61B 34/70; A61B 34/71; A61B 34/74; A61B 34/30;

(Continued)

(56) References Cited

U.S. PATENT DOCUMENTS 2,556,601 A    6/1951  Schofield
2,566,183 A    8/1951  Forss
(Continued)

FOREIGN PATENT DOCUMENTS

CN    101500470    8/2009
CN    102665590    9/2012
(Continued)

OTHER PUBLICATIONS

Mayo Clinic, Robotic Surgery, https://www.mayoclinic.org/tests-procedures/robotic-surgery/about/pac-20394974?p=1, downloaded from the internet on Jul. 12, 2018, 2 pp.

*Primary Examiner* — Matthew Kremer
*Assistant Examiner* — Avery M Foley
(74) *Attorney, Agent, or Firm* — Knobbe, Martens, Olson & Bear, LLP (57) ABSTRACT

Various exemplary drive apparatuses and associated methods are disclosed for driving an elongated member, e.g., a guidewire or catheter. An exemplary drive apparatus for driving an elongated member may include a rotational component configured to apply a torque to the elongated member, where the rotational component is positioned a first distance away from an insertion site along the elongated member. The drive apparatus may further include a rotational support configured to apply an assistance torque to the elongated member. The rotational support may be positioned a second distance from the rotational component along the elongated member that is larger than the first distance.

24 Claims, 3 Drawing Sheets

(58) Field of Classification Search
CPC ....... A61B 2034/301; A61B 2034/302; A61M 25/09041; A61M 25/0905
See application file for complete search history.

(56) References Cited

U.S. PATENT DOCUMENTS

| | | | |
|---|---|---|---|
| 2,623,175 A | 12/1952 | Finke | |
| 2,730,699 A | 1/1956 | Gratian | |
| 2,884,808 A | 5/1956 | Mueller | |
| 3,294,183 A | 12/1966 | Riley et al. | |
| 3,472,083 A | 10/1969 | Schnepel | |
| 3,513,724 A | 5/1970 | Box | |
| 3,595,074 A | 7/1971 | Johnson | |
| 3,734,207 A | 5/1973 | Fishbein | |
| 3,739,923 A | 6/1973 | Totsuka | |
| 3,784,031 A | 1/1974 | Nitu | |
| 3,921,536 A | 11/1975 | Savage | |
| 3,926,386 A | 12/1975 | Stahmann | |
| 4,141,245 A | 2/1979 | Brandstetter | |
| 4,241,884 A | 12/1980 | Lynch | |
| 4,243,034 A | 1/1981 | Brandt | |
| 4,351,493 A | 9/1982 | Sonnek | |
| 4,357,843 A | 11/1982 | Peck et al. | |
| 4,384,493 A | 5/1983 | Grunbaum | |
| 4,507,026 A | 3/1985 | Lund | |
| 4,530,471 A | 7/1985 | Inoue | |
| 4,555,960 A | 12/1985 | King | |
| 4,688,555 A | 6/1987 | Wardle | |
| 4,745,908 A | 5/1988 | Wardle | |
| 4,784,150 A | 11/1988 | Voorhies et al. | |
| 4,857,058 A | 8/1989 | Payton | |
| 4,907,168 A | 3/1990 | Boggs | |
| 4,945,790 A | 8/1990 | Golden | |
| 5,207,128 A | 5/1993 | Albright | |
| 5,234,428 A | 8/1993 | Kaufman | |
| 5,256,150 A | 10/1993 | Quiachon et al. | |
| 5,277,085 A | 1/1994 | Tanimura et al. | |
| 5,350,101 A | 9/1994 | Godlewski | |
| 5,398,691 A | 3/1995 | Martin et al. | |
| 5,408,409 A | 4/1995 | Glassman et al. | |
| 5,426,687 A | 6/1995 | Goodall et al. | |
| 5,507,725 A | 4/1996 | Savage et al. | |
| 5,524,180 A * | 6/1996 | Wang | B60R 21/0132 600/117 |
| 5,559,294 A | 9/1996 | Hoium et al. | |
| 5,631,973 A | 5/1997 | Green | |
| 5,709,661 A | 1/1998 | Van Egmond | |
| 5,713,946 A | 2/1998 | Ben-Haim | |
| 5,749,362 A | 5/1998 | Funda et al. | |
| 5,767,840 A | 6/1998 | Selker | |
| 5,779,623 A | 7/1998 | Bonnell | |
| 5,792,135 A | 8/1998 | Madhani et al. | |
| 5,855,583 A | 1/1999 | Wang et al. | |
| 5,859,934 A | 1/1999 | Green | |
| 5,876,325 A | 3/1999 | Mizuno et al. | |
| 5,921,968 A | 7/1999 | Lampropoulos et al. | |
| 5,951,475 A | 9/1999 | Gueziec et al. | |
| 5,967,934 A | 10/1999 | Ishida et al. | |
| 6,084,371 A | 7/2000 | Kress et al. | |
| 6,154,000 A | 11/2000 | Rastegar et al. | |
| 6,171,234 B1 | 1/2001 | White et al. | |
| 6,185,478 B1 | 2/2001 | Koakutsu et al. | |
| 6,226,543 B1 | 5/2001 | Gilboa et al. | |
| 6,259,806 B1 | 7/2001 | Green | |
| 6,272,371 B1 | 8/2001 | Shlomo | |
| 6,289,579 B1 | 9/2001 | Viza et al. | |
| 6,394,998 B1 | 5/2002 | Wallace et al. | |
| 6,401,572 B1 | 6/2002 | Provost | |
| 6,424,885 B1 | 7/2002 | Niemeyer et al. | |
| 6,436,107 B1 | 8/2002 | Wang et al. | |
| 6,487,940 B2 | 12/2002 | Hart et al. | |
| 6,491,701 B2 | 12/2002 | Tierney et al. | |
| 6,695,818 B2 | 2/2004 | Wollschlager | |
| 6,726,675 B1 * | 4/2004 | Beyar | A61M 25/0105 600/106 |
| 6,786,896 B1 | 9/2004 | Madhani et al. | |
| 6,827,712 B2 | 12/2004 | Tovey et al. | |
| 7,044,936 B2 | 5/2006 | Harding | |
| 7,155,315 B2 | 12/2006 | Niemeyer et al. | |
| 7,172,580 B2 | 2/2007 | Hruska et al. | |
| 7,276,044 B2 | 10/2007 | Ferry et al. | |
| 7,615,042 B2 | 11/2009 | Beyar et al. | |
| 7,635,342 B2 | 12/2009 | Ferry et al. | |
| 7,766,856 B2 | 8/2010 | Ferry et al. | |
| 7,789,874 B2 | 9/2010 | Yu et al. | |
| 7,938,809 B2 | 5/2011 | Larnpropoulos et al. | |
| 7,974,674 B2 | 7/2011 | Hauck et al. | |
| 7,998,020 B2 | 8/2011 | Kidd et al. | |
| 8,052,636 B2 | 11/2011 | Moll et al. | |
| 8,146,874 B2 | 4/2012 | Yu | |
| 8,157,308 B2 | 4/2012 | Pedersen | |
| 8,182,415 B2 | 5/2012 | Larkin et al. | |
| 8,277,417 B2 | 10/2012 | Fedinec et al. | |
| 8,291,791 B2 | 10/2012 | Light et al. | |
| 8,414,505 B1 | 4/2013 | Weitzner | |
| 8,425,465 B2 | 4/2013 | Nagano | |
| 8,671,817 B1 | 3/2014 | Bogusky | |
| 8,720,448 B2 | 5/2014 | Reis et al. | |
| 8,746,252 B2 | 6/2014 | McGrogan et al. | |
| 8,870,815 B2 * | 10/2014 | Bhat | A61B 1/00147 604/95.01 |
| 8,961,533 B2 | 2/2015 | Stahler et al. | |
| 8,968,333 B2 | 3/2015 | Yu et al. | |
| 8,992,542 B2 | 3/2015 | Hagag et al. | |
| 9,173,713 B2 | 11/2015 | Hart et al. | |
| 9,204,933 B2 | 12/2015 | Reis et al. | |
| 9,314,306 B2 | 4/2016 | Yu | |
| 9,326,822 B2 | 5/2016 | Lewis et al. | |
| 9,408,669 B2 | 8/2016 | Kokish et al. | |
| 9,446,177 B2 | 9/2016 | Millman et al. | |
| 9,452,018 B2 | 9/2016 | Yu | |
| 9,457,168 B2 | 10/2016 | Moll et al. | |
| 9,498,601 B2 | 11/2016 | Tanner et al. | |
| 9,504,604 B2 | 11/2016 | Alvarez | |
| 9,561,083 B2 | 2/2017 | Yu et al. | |
| 9,566,201 B2 | 2/2017 | Yu | |
| 9,622,827 B2 | 4/2017 | Yu et al. | |
| 9,636,184 B2 | 5/2017 | Lee et al. | |
| 9,636,483 B2 | 5/2017 | Hart et al. | |
| 9,668,814 B2 | 6/2017 | Kokish | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,844,412 B2 | 12/2017 | Bogusky et al. | |
| 9,867,635 B2 | 1/2018 | Alvarez et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,143,360 B2 | 12/2018 | Roelle et al. | |
| 10,145,747 B1 | 12/2018 | Lin et al. | |
| 10,159,532 B1 | 12/2018 | Ummalaneni et al. | |
| 10,213,264 B2 | 2/2019 | Tanner et al. | |
| 10,299,870 B2 | 5/2019 | Connolly et al. | |
| 10,426,559 B2 | 10/2019 | Graetzel et al. | |
| 10,434,660 B2 | 10/2019 | Meyer | |
| 10,464,209 B2 | 11/2019 | Ho et al. | |
| 10,470,830 B2 | 11/2019 | Hill | |
| 10,482,599 B2 | 11/2019 | Mintz et al. | |
| 10,517,692 B2 | 12/2019 | Eyre et al. | |
| 10,524,866 B2 | 1/2020 | Srinivasan | |
| 2001/0042643 A1 | 11/2001 | Krueger et al. | |
| 2002/0045905 A1 | 4/2002 | Gerbi et al. | |
| 2002/0098938 A1 | 7/2002 | Milbourne et al. | |

(56) References Cited

U.S. PATENT DOCUMENTS

| | | |
|---|---|---|
| 2002/0100254 A1 | 8/2002 | Dharssi |
| 2002/0107573 A1* | 8/2002 | Steinberg ......... A61B 17/00234 623/17.12 |
| 2002/0117017 A1 | 8/2002 | Bernhardt et al. |
| 2002/0161355 A1 | 10/2002 | Wollschlager |
| 2002/0161426 A1 | 10/2002 | Lancea |
| 2002/0177789 A1 | 11/2002 | Ferry et al. |
| 2003/0056561 A1 | 3/2003 | Butscher et al. |
| 2004/0015053 A1 | 1/2004 | Bieger |
| 2004/0152972 A1 | 8/2004 | Hunter |
| 2004/0243147 A1 | 12/2004 | Lipow |
| 2004/0254566 A1* | 12/2004 | Plicchi ................ A61B 34/70 606/1 |
| 2005/0004579 A1 | 1/2005 | Schneider et al. |
| 2005/0183532 A1 | 8/2005 | Najaf et al. |
| 2005/0222554 A1 | 10/2005 | Wallace et al. |
| 2006/0025676 A1 | 2/2006 | Viswanathan et al. |
| 2006/0041245 A1 | 2/2006 | Ferry |
| 2006/0111692 A1 | 5/2006 | Hlavka et al. |
| 2006/0146010 A1 | 7/2006 | Schneider |
| 2006/0161045 A1 | 7/2006 | Merril et al. |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0013336 A1 | 1/2007 | Nowlin et al. |
| 2007/0060879 A1 | 3/2007 | Weitzner et al. |
| 2007/0100254 A1 | 5/2007 | Murakami |
| 2007/0112355 A1 | 5/2007 | Salahieh |
| 2007/0119274 A1 | 5/2007 | Devengenzo et al. |
| 2007/0149946 A1 | 6/2007 | Viswanathan |
| 2007/0191177 A1 | 8/2007 | Nagai et al. |
| 2007/0239028 A1 | 10/2007 | Houser |
| 2007/0245175 A1 | 10/2007 | Zheng et al. |
| 2007/0299427 A1 | 12/2007 | Yeung et al. |
| 2008/0039255 A1 | 2/2008 | Jinno et al. |
| 2008/0046122 A1 | 2/2008 | Manzo et al. |
| 2008/0065103 A1 | 3/2008 | Cooper et al. |
| 2008/0147011 A1 | 6/2008 | Urmey |
| 2008/0177285 A1 | 7/2008 | Brock et al. |
| 2008/0214925 A1 | 9/2008 | Wilson et al. |
| 2008/0243064 A1 | 10/2008 | Stahler et al. |
| 2008/0245946 A1 | 10/2008 | Yu |
| 2008/0249536 A1 | 10/2008 | Stahler et al. |
| 2008/0253108 A1 | 10/2008 | Yu et al. |
| 2008/0262301 A1 | 10/2008 | Gibbons et al. |
| 2008/0302200 A1 | 12/2008 | Tobey |
| 2009/0082722 A1 | 3/2009 | Munger et al. |
| 2009/0098971 A1 | 4/2009 | Ho et al. |
| 2009/0105645 A1 | 4/2009 | Kidd et al. |
| 2009/0171371 A1 | 7/2009 | Nixon |
| 2009/0247944 A1 | 10/2009 | Kirschenman et al. |
| 2009/0248039 A1 | 10/2009 | Cooper et al. |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0130923 A1 | 5/2010 | Cleary et al. |
| 2010/0130987 A1 | 5/2010 | Wenderow et al. |
| 2010/0175701 A1 | 7/2010 | Reis et al. |
| 2010/0204646 A1 | 8/2010 | Plicchi et al. |
| 2010/0210923 A1 | 8/2010 | Li et al. |
| 2010/0248177 A1 | 9/2010 | Mangelberger et al. |
| 2010/0274078 A1 | 10/2010 | Kim et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028991 A1 | 2/2011 | Ikeda et al. |
| 2011/0130718 A1 | 6/2011 | Kidd et al. |
| 2011/0147030 A1 | 6/2011 | Blum et al. |
| 2011/0152880 A1* | 6/2011 | Alvarez ............. A61M 25/0138 606/130 |
| 2011/0238083 A1 | 9/2011 | Moll et al. |
| 2011/0261183 A1 | 10/2011 | Ma et al. |
| 2011/0277775 A1 | 11/2011 | Holop et al. |
| 2011/0288573 A1 | 11/2011 | Yates et al. |
| 2011/0306836 A1 | 12/2011 | Online et al. |
| 2012/0071621 A1 | 3/2012 | Yu |
| 2012/0071894 A1 | 3/2012 | Tanner et al. |
| 2012/0071895 A1 | 3/2012 | Stahler et al. |
| 2012/0143226 A1 | 6/2012 | Belson et al. |
| 2012/0150154 A1* | 6/2012 | Brisson .................. A61B 17/00 606/1 |
| 2012/0186194 A1 | 7/2012 | Schlieper |
| 2012/0191107 A1 | 7/2012 | Tanner et al. |
| 2012/0232476 A1 | 9/2012 | Bhat et al. |
| 2012/0239012 A1 | 9/2012 | Laurent et al. |
| 2012/0241576 A1 | 9/2012 | Yu |
| 2012/0277730 A1* | 11/2012 | Salahieh ............. A61B 1/00135 604/527 |
| 2012/0283747 A1 | 11/2012 | Popovic |
| 2013/0018400 A1 | 1/2013 | Milton et al. |
| 2013/0144116 A1 | 6/2013 | Cooper et al. |
| 2013/0231678 A1* | 9/2013 | Wenderow ............ A61B 34/30 606/130 |
| 2013/0269109 A1 | 10/2013 | Yu |
| 2013/0304084 A1 | 11/2013 | Beira et al. |
| 2013/0317519 A1 | 11/2013 | Romo et al. |
| 2013/0345519 A1 | 12/2013 | Piskun et al. |
| 2014/0000411 A1 | 1/2014 | Shelton, IV et al. |
| 2014/0066944 A1 | 3/2014 | Taylor et al. |
| 2014/0069437 A1 | 3/2014 | Reis et al. |
| 2014/0142591 A1 | 5/2014 | Alvarez et al. |
| 2014/0166023 A1 | 6/2014 | Kishi |
| 2014/0171778 A1 | 6/2014 | Tsusaka |
| 2014/0222019 A1 | 8/2014 | Brudnick |
| 2014/0276233 A1 | 9/2014 | Murphy |
| 2014/0276389 A1 | 9/2014 | Walker |
| 2014/0276391 A1 | 9/2014 | Yu |
| 2014/0276394 A1 | 9/2014 | Wong et al. |
| 2014/0276594 A1 | 9/2014 | Tanner et al. |
| 2014/0276647 A1 | 9/2014 | Yu |
| 2014/0276935 A1 | 9/2014 | Yu |
| 2014/0276936 A1 | 9/2014 | Kokish et al. |
| 2014/0277333 A1 | 9/2014 | Lewis et al. |
| 2014/0277334 A1 | 9/2014 | Yu et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0051592 A1 | 2/2015 | Kintz |
| 2015/0090063 A1 | 4/2015 | Lantermann et al. |
| 2015/0101442 A1 | 4/2015 | Romo |
| 2015/0119638 A1 | 4/2015 | Yu et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0164594 A1 | 6/2015 | Romo et al. |
| 2015/0164596 A1 | 6/2015 | Romo |
| 2015/0182250 A1 | 7/2015 | Conlon et al. |
| 2015/0231364 A1 | 8/2015 | Blanchard |
| 2015/0297864 A1 | 10/2015 | Kokish et al. |
| 2015/0327939 A1 | 11/2015 | Kokish et al. |
| 2015/0335480 A1 | 11/2015 | Alvarez et al. |
| 2015/0374445 A1 | 12/2015 | Gombert et al. |
| 2016/0000512 A1 | 1/2016 | Gombert et al. |
| 2016/0001038 A1 | 1/2016 | Romo et al. |
| 2016/0100896 A1 | 4/2016 | Yu |
| 2016/0157945 A1 | 6/2016 | Madhani |
| 2016/0166234 A1 | 6/2016 | Zhang |
| 2016/0235946 A1 | 8/2016 | Lewis et al. |
| 2016/0270865 A1 | 9/2016 | Landey et al. |
| 2016/0287279 A1 | 10/2016 | Bovay et al. |
| 2016/0296294 A1 | 10/2016 | Moll et al. |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0354582 A1 | 12/2016 | Yu et al. |
| 2016/0374541 A1 | 12/2016 | Agrawal et al. |
| 2017/0007337 A1 | 1/2017 | Dan |
| 2017/0071684 A1 | 3/2017 | Kokish et al. |
| 2017/0100199 A1 | 4/2017 | Yu et al. |
| 2017/0105804 A1 | 4/2017 | Yu |
| 2017/0119413 A1 | 5/2017 | Romo |

(56) References Cited

U.S. PATENT DOCUMENTS

| | | |
|---|---|---|
| 2017/0119481 A1 | 5/2017 | Romo et al. |
| 2017/0151028 A1 | 6/2017 | Ogawa et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209672 A1 | 7/2017 | Hart et al. |
| 2017/0252540 A1 | 9/2017 | Weitzner et al. |
| 2017/0281049 A1 | 10/2017 | Yamamoto |
| 2017/0290631 A1 | 10/2017 | Lee et al. |
| 2017/0296784 A1 | 10/2017 | Kokish |
| 2017/0312481 A1 | 11/2017 | Covington et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042464 A1 | 2/2018 | Arai |
| 2018/0049792 A1 | 2/2018 | Eckert |
| 2018/0056044 A1 | 3/2018 | Choi et al. |
| 2018/0104820 A1 | 4/2018 | Troy et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0296299 A1 | 10/2018 | Iceman |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0083183 A1 | 3/2019 | Moll et al. |
| 2019/0105776 A1 | 4/2019 | Ho et al. |
| 2019/0105785 A1 | 4/2019 | Meyer |
| 2019/0107454 A1 | 4/2019 | Lin |
| 2019/0110839 A1 | 4/2019 | Rafii-Tari et al. |
| 2019/0110843 A1 | 4/2019 | Ummalaneni et al. |
| 2019/0151148 A1 | 4/2019 | Alvarez et al. |
| 2019/0142537 A1 | 5/2019 | Covington et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175287 A1 | 6/2019 | Hill |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre |
| 2019/0216576 A1 | 7/2019 | Eyre |
| 2019/0223974 A1 | 7/2019 | Romo |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0328213 A1 | 10/2019 | Landey et al. |
| 2019/0336238 A1 | 11/2019 | Yu |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Alvarez |
| 2019/0380787 A1 | 12/2019 | Ye |
| 2019/0380797 A1 | 12/2019 | Yu |
| 2020/0000530 A1 | 1/2020 | DeFonzo |
| 2020/0000533 A1 | 1/2020 | Schuh |
| 2020/0022767 A1 | 1/2020 | Hill |

FOREIGN PATENT DOCUMENTS

| | | |
|---|---|---|
| DE | 19649082 | 1/1998 |
| DE | 102004020465 | 9/2005 |
| EP | 1 442 720 | 8/2004 |
| EP | 2 567 670 | 3/2013 |
| EP | 3 025 630 | 6/2016 |
| JP | 07-136173 | 5/1995 |
| JP | 2009-139187 | 6/2009 |
| JP | 2010-046384 | 6/2009 |
| WO | WO 02/074178 | 9/2002 |
| WO | 03086190 A1 | 10/2003 |
| WO | WO 07/146987 | 12/2007 |
| WO | WO 09/092059 | 7/2009 |
| WO | WO 11/005335 | 1/2011 |
| WO | WO 12/037506 | 3/2012 |
| WO | WO 13/179600 | 12/2013 |
| WO | WO 15/127231 | 8/2015 |
| WO | WO 17/059412 | 4/2017 |
| WO | WO 17/0151993 | 9/2017 |

\* cited by examiner

ROTATIONAL SUPPORT FOR AN ELONGATE MEMBER

CROSS-REFERENCE TO RELATED APPLICATION

This application is a continuation of U.S. patent application Ser. No. 13/833,531, entitled "ROTATIONAL SUPPORT FOR AN ELONGATE MEMBER" filed Mar. 15, 2013, the entirety of which is herein incorporated by reference for all purposes.

BACKGROUND

Robotic interventional systems and devices are well suited for performing minimally invasive medical procedures as opposed to conventional techniques wherein the patient's body cavity is open to permit the surgeon's hands access to internal organs. However, advances in technology have led to significant changes in the field of medical surgery such that less invasive surgical procedures, in particular, minimally invasive surgery (MIS), are increasingly popular.

A MIS is generally defined as a procedure that is performed by entering the body through the skin, a body cavity, or an anatomical opening utilizing small incisions rather than large, open incisions in the body. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments.

MIS apparatus and techniques have advanced to the point where an insertion and rolling motion of components of an elongated component such as a catheter instrument, e.g., a catheter sheath and associated guidewire, are generally controllable by selectively operating rollers or other mechanisms for generally gripping the component. Due to the length and complexity of catheter instruments and components thereof, rotation of the catheter may be generally difficult to control.

Accordingly, there is a need in the art for systems and methods for inserting and rolling catheter components that address or solve the above problems.

SUMMARY

An exemplary method of driving an elongated member, e.g., a guidewire or catheter, merely as examples, may include applying a first torque to the elongated member with a rotational component that is positioned a first distance away from an insertion site along the elongated member. The exemplary method may further include applying an assistance torque to the elongated member with a rotational support positioned a second distance away from an insertion site along the elongated member, where the second distance is larger than the first distance.

An exemplary drive apparatus for driving an elongated member may include a rotational component configured to apply a torque to the elongated member, where the rotational component is positioned a first distance away from an insertion site along the elongated member. The drive apparatus may further include a rotational support configured to apply an assistance torque to the elongated member. The rotational support may be positioned a second distance from the rotational component along the elongated member that is larger than the first distance.

BRIEF DESCRIPTION OF THE DRAWINGS

While the claims are not limited to the illustrated embodiments, an appreciation of various aspects is best gained through a discussion of various examples thereof. Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limiting or restricting to the precise form and configuration shown in the drawings and disclosed in the following detailed description. Exemplary embodiments of the present invention are described in detail by referring to the drawings as follows.

DETAILED DESCRIPTION

Referring now to the drawings, illustrative embodiments are shown in detail. Although the drawings represent the embodiments, the drawings are not necessarily to scale and certain features may be exaggerated to better illustrate and explain an innovative aspect of an embodiment. Further, the embodiments described herein are not intended to be exhaustive or otherwise limit or restrict the invention to the precise form and configuration shown in the drawings and disclosed in the following detailed description.

Figure 1:
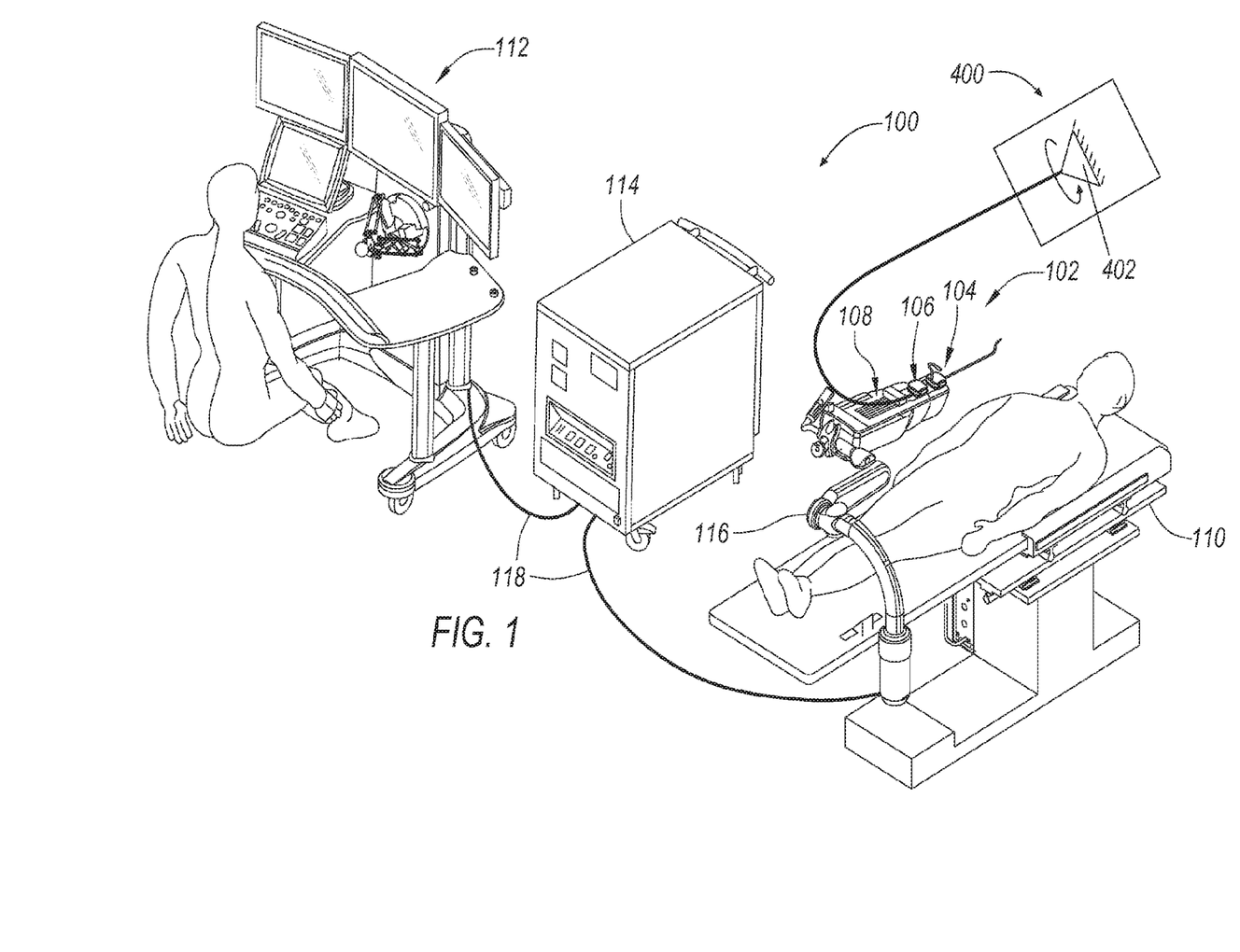
FIG. 1 is an illustration of a robotically controlled surgical system, according to one exemplary illustration.

Referring to FIG. 1, a robotically controlled surgical system 100 is illustrated in which an apparatus, a system, and/or method may be implemented according to various exemplary illustrations. System 100 may include a robotic catheter assembly 102 having a robotic or first or outer steerable complement, otherwise referred to as a sheath instrument 104 (generally referred to as "sheath" or "sheath instrument") and/or a second or inner steerable component, otherwise referred to as a robotic catheter or guide or catheter instrument 106 (generally referred to as "catheter" or "catheter instrument"). Catheter assembly 102 is controllable using a robotic instrument driver 108 (generally referred to as "instrument driver").

Moreover, as described further below in regard to FIGS. 2 and 3, a rotational support 400 may be provided which is configured to provide an assistance torque to an elongate member that is part of the catheter assembly 102. For example, a rotational support 400 may be configured to provide an assistance torque to a guidewire inserted coaxially into the catheter 102 assembly, e.g., within a catheter sheath. The rotational support 400 may be used to support an elongated member such as the guidewire rotationally, to allow a greater degree of control over the rotation of the elongate member.

During use, a patient is positioned on an operating table or surgical bed 110 (generally referred to as "operating table") to which robotic instrument driver 108 may be coupled or mounted. In the illustrated example, system 100 includes an operator workstation 112, an electronics rack 114 and associated bedside electronics box (not shown), a setup joint mounting brace 116, and instrument driver 108. A surgeon is seated at operator workstation 112 and can monitor the surgical procedure, patient vitals, and control one or more catheter devices. Operator workstation 112 may include a computer monitor to display a three dimensional object, such as a catheter instrument or component thereof, e.g., a guidewire, catheter sheath. Moreover, a catheter instrument may be displayed within or relative to a three dimensional space, such as a body cavity or organ, e.g., a chamber of a patient's heart. In one example, an operator uses a computer mouse to move a control point around the display to control the position of catheter instrument.

System components may be coupled together via a plurality of cables or other suitable connectors 118 to provide for data communication, or one or more components may be equipped with wireless communication components to reduce or eliminate cables 118. Communication between components may also be implemented over a network or over the internet. In this manner, a surgeon or other operator may control a surgical instrument while being located away from or remotely from radiation sources, thereby decreasing radiation exposure. Because of the option for wireless or networked operation, the surgeon may even be located remotely from the patient in a different room or building.

Figure 2:
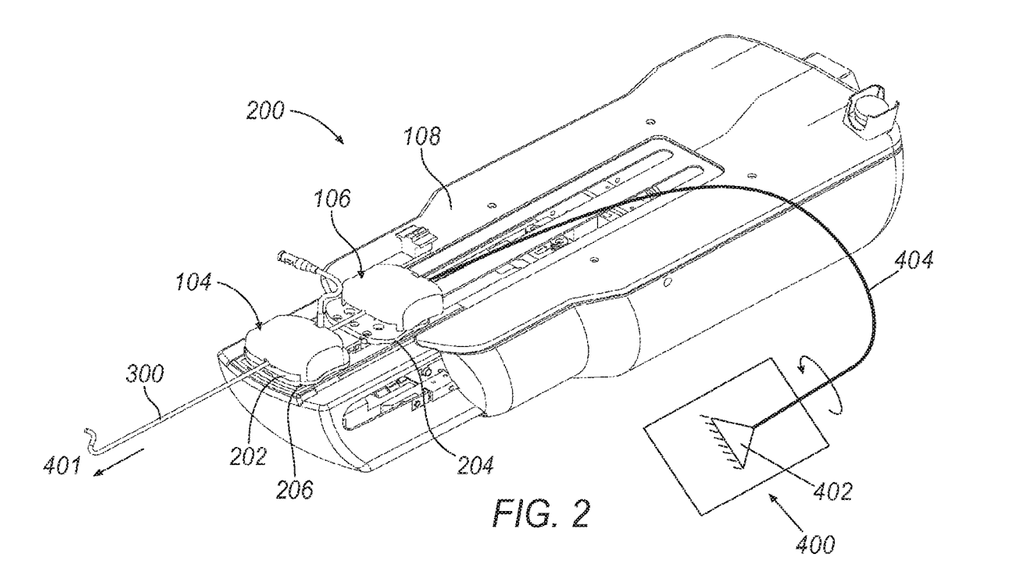
FIG. 2 is an illustration of an exemplary catheter assembly of the surgical system of FIG. 1.

Referring now to FIG. 2, an exemplary drive assembly 200 is shown in further detail, including sheath instrument 104 and the associated guide or catheter instrument 106 mounted to mounting plates 202, 204 on a top portion of instrument driver 108. During use, catheter instrument 106 is inserted within a central lumen of sheath instrument 104 such that instruments 104, 106 are arranged in a coaxial manner. Although instruments 104, 106 are arranged coaxially, movement of each instrument 104, 106 can be controlled and manipulated independently. For this purpose, motors within instrument driver 108 are controlled such that carriages coupled to each of the instruments 104, 160 may allow the instruments 104, 106 to be driven forwards and backwards along the driver 108, e.g., with mounting plates securing the instruments to the driver 108 on bearings. As a result, a catheter 300 coupled to guide catheter instrument 106 and sheath instrument 104 can be controllably manipulated while inserted into the patient, as will be further illustrated. Additional instrument driver 108 motors (not shown in FIG. 2) may be activated to control bending of the catheter as well as the orientation of the distal tips thereof, including tools mounted at the distal tip. Sheath catheter instrument 106 is configured to move forward and backward for effecting an axial motion of the catheter, e.g., to insert and withdraw the catheter from a patient, respectively. For example, the catheter 300 is configured to be inserted and removed from the patient's body at an insertion site 401.

At least one of the instruments 104, 106 may apply a torque to an elongated member included in the catheter 300. For example, a guidewire 404 may be inserted into the instruments 104, 106 for guiding the catheter 300. In one exemplary illustration, the instrument 106 applies a torque to the guidewire 404, e.g., to impart a rotational motion for guidance of the catheter. The rotational support 400, which is positioned further away from the insertion site 401 than the instrument 106, may apply an assistance torque to the guidewire 404, and end of which is attached to the rotational support 400 at a fixture 402. In some exemplary approaches described further below, the assistance torque may be a larger amount than that applied by the instrument 106. In another example, the assistance torque is applied as a "coarse" adjustment relative to torque being applied by the instrument 106, wherein torque is applied to the guidewire 404 in relatively large amounts via the rotational support 400. By contrast, torque may be more finely adjusted by the instrument 106. In this manner, the application of torque using the rotational support 400 and the instrument 106 is similar to a physician using two hands to rotate the wire, where the hand closest to the operating/insertion site makes fine torque adjustments, perhaps with only the fingertips, while the rearward hand makes relatively larger "gross" torque adjustments with the hand grasping the wire. Moreover, the rotational support 400 may have a relatively tighter grip on the rearward end of the guidewire, as will be described further below.

Figure 3:
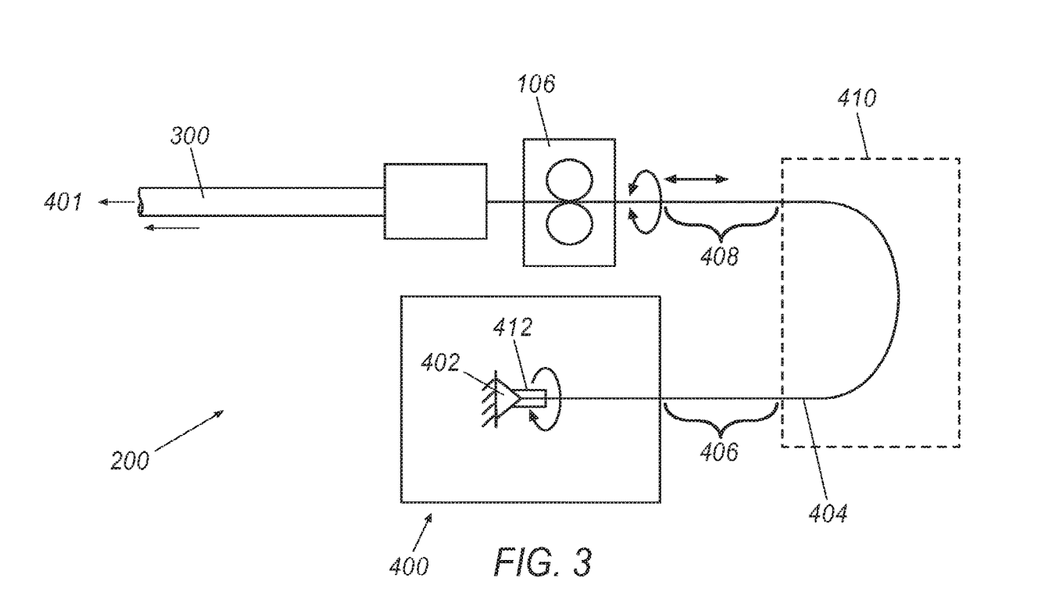
FIG. 3 is a schematic view of the exemplary illustration of an exemplary catheter assembly of the surgical system of FIGS. 1 and 2.

Referring now to FIG. 3, the exemplary drive assembly 200 is illustrated in further detail. The rotational component or instrument 106, as noted above, may be configured to apply a torque to the elongated member, e.g., a guidewire 404, while the rotational support 400 is configured to apply an assistance torque to the elongated member. The guidewire 404 includes a turned portion 406 which is wrapped approximately 180 degrees with respect to another portion 408 that is aligned for insertion into the instrument 106. The turning of the guidewire 404 may generally facilitate insertion of the guidewire 404, i.e., by placing the end 408 of the guidewire 404 relatively close to the instrument 106. Accordingly, during insertion of the guidewire 404 into the instrument 106, the lengths of the turned portion 406 and the aligned portion may decrease as a greater length overall of the guidewire 404 is inserted. As a result of the turning of the wire, e.g., to the 180 degree orientation, the rotational support 400 does not require movement relative to the rotational component 106. Alternatively, if the elongate member were oriented straight, i.e., such that the entire elongate member were aligned along the insertion axis of the instrument 106, the rotational support 400 would be required to mount to a moveable carriage to allow insertion and retraction of the elongate member.

The turning of the guidewire 404 may also facilitate the use of an intermediate support 410 for the guidewire 404 in between the rotational support 400 and the instrument 106. In particular, to the extent there is any different in torque or rotational movement being applied to the guidewire 404 by the rotational support 400 on the one hand and the instrument 106 on the other, an intermediate support 410 may generally prevent the guidewire 404 from twisting. In one exemplary approach, the intermediate support 410 includes two planar members generally sandwiching the guidewire 404 therebetween. Accordingly, the guidewire 404 is generally forced to remain substantially in a single plane. Moreover, the use of two planar members may generally freely permit movement of the guidewire 404 as a result of insertion, i.e., taking up more of the slack in the guidewire. As another example, the guidewire 404 may be placed in a track (not shown). As yet another example, one or more weights (not shown) may be applied or secured to the guidewire 404, e.g., along a length of the guidewire 404 intermediate the rotational support 400 and the instrument 106, to inhibit vertical movement of the guidewire 404, thereby preventing the guidewire 404 from twisting upon itself.

The rotational support 400 may generally anchor or fix the end to an infinitely rotatable support 402. For example, the support 402 may be a collet comprising a sleeve 412 that extends from the end of the elongated member, i.e., the guidewire, along a length of the elongated member. The end of the guidewire 404 may thereby be generally anchored to the rotational support 400. Moreover, the end of the guidewire may be generally gripped or anchored in a far more aggressive manner than generally possible for the instrument 106, as the instrument 106 must generally be configured to apply fine torque adjustments to the guidewire 404. Moreover, the instrument 106 must generally not damage the guidewire 406. By contrast, the end of the guidewire 404 may be anchored or clamped within the rotational support 400 as aggressively as possible to maintain a relatively firm grip on the guidewire. The end of the guidewire 404 is generally permanently fixed to the rotational support 400, and can be clamped aggressively, without any regard for damage to the guidewire 404 that the instrument 106, on the other hand, must generally avoid. Moreover, in one exemplary illustration, the end of the guidewire 404 is grabbed by a disposable component through a sterile drape (not shown in FIG. 3), allowing the rotational support 400 to remain under the sterile drape. Accordingly, reuse of the rotational support 400 for subsequent procedures is generally possible.

In some exemplary approaches, as noted above the rotational support 400 may be configured to adjust the assistance torque in relatively large increments as a "gross" adjustment, while the rotational component, i.e., instrument 106, is configured to apply torque adjustments in smaller increments as a "fine" adjustment. Moreover, the rotational support 400 may include any rotational device that is convenient, e.g., an infinitely rotatable tool such as a geared wheel (not shown) or other mechanism configured to rotate continuously. Accordingly, the rotational support 400 need not be limited to any particular rotational range of motion. Moreover, the use of an infinitely rotatable tool also facilitates the generally permanent clamping of the end of the guidewire 404, since there is no need to release and re-grip the guidewire 404.

In another exemplary illustration, the rotational support 400 may be used to apply a proportionally greater rotational movement or torque to an elongate member, e.g., guidewire 404. In some exemplary approaches, the rotational component, i.e., instrument 106, may generally be used to selectively release the guidewire 404 after the application of a relatively larger amount of rotation and/or torque that is needed in a given procedure. More specifically, the rotational support 400 may be used to "wind up" the guidewire to a magnitude, e.g., a torque, that generally exceeds a torque expected for a given procedure or movement of the elongate member. Subsequently, the instrument 106 may selectively "deploy" the torque present in the length of the elongate member between the instrument 106 and the rotational support 400 to the length of the elongate member in between the instrument 106 and an insertion site, e.g., insertion site 401.

In another example, for each magnitude of rotation applied to the guidewire 404 by the instrument 106, the rotational support 400 may rotate a larger magnitude. In one example, the rotational support 400 turns four times more than the corresponding instrument 106. The particular relationship between the magnitude of the rotation of the rotation support 400 and the instrument 106 will be dependent on the wire length and type. For example, where a larger length of the elongated member, e.g., guidewire 400 is employed, the greater length may allow a larger difference in rotation between the rotational support 400 and the instrument 106. Additionally, where a more delicate elongate member is employed, a comparatively smaller difference in rotation between the rotational support 400 and the instrument 106 may be employed in view of the increased likelihood of damaging the elongate member.

Figure 4:
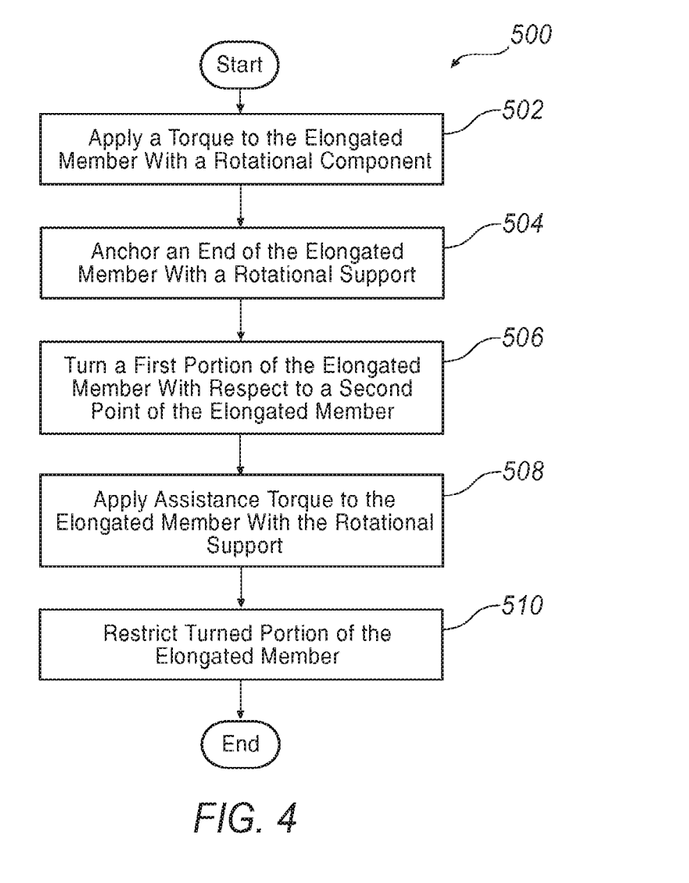
FIG. 4 is process flow diagram for an exemplary method of driving an elongated member.

Referring now to FIG. 4, an exemplary process 400 of driving an elongated member is described. Process 400 may begin at block 402, where a first torque is applied to an elongate member with a rotational component. For example, as described above a first torque may be applied to an elongate member, e.g., guidewire 404, with a rotational component, e.g., instrument 106. The instrument 106 may be positioned a first distance away from an insertion site along the elongated member, such that it is closer to the insertion site than an associated rotational support, e.g., rotational support 400. Process 400 may then proceed to block 404.

At block 404, an end of the elongate member may be anchored with the rotational support. For example, an end of a guidewire 404 may be anchored to a collet 402 or within a sleeve 412 that is configured to secure the end of the guidewire 404. Moreover, the elongate member may be generally deformed within the collet 402 or sleeve 412, as the guidewire 400 need not be handled delicately since the end of the guidewire 404 adjacent the rotational support 400 and an adjacent length is not expected to be used for insertion or to be handled by the instrument 106. As described above, the end of the elongate member, e.g., guidewire 404, may be received within a sleeve 412 that extends along a length of the guidewire 404, thereby facilitating a generally secure grip and allowing application of generally greater torque and/or rotational magnitude than is generally possible with the instrument 106. Process 400 may then proceed to block 406.

At block 406, a first portion of the elongate member may be turned with respect to a second portion of the elongate member. For example, as described above a first portion 406 of a guidewire 404 may be turned such that it is rotated approximately 180 degrees with respect to a second portion 408 that is aligned for insertion into the rotational component, i.e., instrument 106.

Proceeding to block 408, an assistance torque or rotation may be applied to the elongate member with a rotational support, e.g., rotational support 400. The rotational support 400, in some examples as described above, may be positioned generally further away from an insertion site along the elongated member than the rotational component, i.e., the instrument 106. In some exemplary approaches, the assistance torque and/or the rotational movement applied by the rotational support 400 may be greater than the torque and/or rotational movement applied by the rotational component, e.g., instrument 106. In some examples, the rotational component, e.g., instrument 106, may be used to selectively release a portion of the assistance torque being applied by the rotational support 400. More specifically, the rotational support 400 may apply an assistance torque or rotational movement that is relatively larger than expected to be applied by the instrument 106. The instrument 106 may then release a portion of the rotational movement and/or the torque to the portion of the elongate member between the instrument 106 and the insertion site. The assistance torque may function, in some examples, as a coarse torque adjustment with respect to a relatively fine torque adjustment applied by the rotational component, i.e., the instrument 106. For example, the assistance torque may be adjusted or applied in larger increments than the torque applied by the rotational component, i.e., the instrument 106. The rotational support 400 may also have a generally infinite rotational range of motion, e.g., with a generally circular wheel or other continuously rotatable tool, thereby permitting continuous rotational movement to be applied to any degree without requiring releasing or re-gripping the elongate member.

Proceeding to block 410, a turned portion of the elongate member may be restricted, e.g., to inhibit or prevent twisting of the elongate member. For example, as described above a curved portion of the guidewire 404, i.e., extending between a turned portion 406 and an aligned portion 408 of the guidewire may be kept substantially within a predetermined plane. The restriction of the elongate member may be accomplished using corresponding planar members 410 that may be used to generally trap the elongate member, e.g., a guidewire, therebetween, thereby generally preventing movement of the elongate member outside of the plane defined between the two planar members. Moreover, movement of the guidewire 404 within the defined plane may generally be freely allowed, resulting in a minimal restriction on the guidewire 404 that does not overly interfere with the movement of the guidewire 404, e.g., during insertion.

Operator workstation 112, electronics rack 114, drive apparatus 200, and/or rotational support 400 may include a computer or a computer readable storage medium implementing the operation of drive and implementing the various methods and processes described herein, e.g., process 1300. In general, computing systems and/or devices, such as the processor and the user input device, may employ any of a number of computer operating systems, including, but by no means limited to, versions and/or varieties of the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OS X and iOS operating systems distributed by Apple Inc. of Cupertino, Calif., and the Android operating system developed by the Open Handset Alliance.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

The exemplary illustrations are not limited to the previously described examples. Rather, a plurality of variants and modifications are possible, which also make use of the ideas of the exemplary illustrations and therefore fall within the protective scope. Accordingly, it is to be understood that the above description is intended to be illustrative and not restrictive.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "the," etc. should be read to recite one or more of the indicated elements unless a claim recites an explicit limitation to the contrary.

What is claimed is:

1. A method of robotically driving an elongate member, the method comprising:
   inserting the elongate member into a robotically-controlled rotational component;
   applying a first torque to the elongate member about a longitudinal axis of the elongate member with the robotically-controlled rotational component positioned a first distance away from an insertion site along the elongate member;
   applying a second torque to the elongate member about the same longitudinal axis of the elongate member with a robotically-controlled rotational support positioned a second distance away from the insertion site along the elongate member, and wherein the second distance is longer than the first distance, wherein the robotically-controlled rotational support applies the second torque independently from the robotically-controlled rotational component; and
   decreasing a length of a portion of the elongate member between the robotically-controlled rotational component and the robotically-controlled rotational support to insert the elongate member into the insertion site.

2. The method of claim 1, wherein the second torque is greater than the first torque.

3. The method of claim 1, wherein the second torque is a coarse torque adjustment and the first torque is a fine torque adjustment.

4. The method of claim 1, further comprising:
   adjusting the second torque in a first increment; and
   adjusting the first torque in a second increment smaller than the first increment.

5. The method of claim 1, further comprising anchoring an end of the elongate member with the rotational support.

6. The method of claim 5, wherein anchoring the end of the elongate member includes deforming the elongate member adjacent the end.

7. The method of claim 1, further comprising receiving an end of the elongate member within a sleeve extending from the end of the elongate member along a length of the elongate member.

8. The method of claim 1, wherein the portion of the elongate member positioned between the rotational component and the rotational support changes length during insertion and retraction of the elongate member without relative movement between the rotational component and rotational support.

9. The method of claim 1, wherein robotically driving the elongate member comprises robotically driving a guidewire.

10. The method of claim 9, wherein the rotational support applies the second torque to the guidewire while the guidewire is inserted coaxially into a catheter.

11. The method of claim 1, further comprising selectively releasing a portion of the second torque with the rotational component.

12. The method of claim 1, further comprising applying a force to the elongate member with an intermediate member located between the rotational support and the rotational component to restrict twisting of the elongate member.

13. The method of claim 1, wherein the rotational support is infinitely rotatable.

14. The method of claim 1, further comprising: turning a first portion of the elongate member relative to a second portion of the elongate member.

15. The method of claim 14, wherein the first portion of the elongate member is turned 180 degrees from the second portion of the elongate member.

16. The method of claim 1, wherein a first portion of the elongate member is aligned with the insertion site and a second portion is turned with respect to the first portion.

17. The method of claim 16, wherein the second portion is turned 180 degrees with respect to the first portion.

18. The method of claim 1, further comprising:
   aligning a first portion of the elongate member with an insertion axis, wherein the first portion is between the robotically-controlled rotational component and the robotically-controlled rotational support;
   turning a second portion of the elongate member relative to the first portion so that the second portion is not aligned with the insertion axis, wherein the second portion is between the robotically-controlled rotational component and the robotically-controlled rotational support; and
   shortening a length of the second portion of the elongate member to insert the elongate member into the insertion site.

19. The method of claim 1, further comprising inserting the elongate member into the robotically-controlled rotational support.

20. The method of claim 1, further comprising:
   gripping the elongate member with the robotically-controlled rotational component; and
   releasing the elongate member with the robotically-controlled rotational component.

21. The method of claim 1, further comprising applying axial motion to the elongate member to move the elongate member relative to the robotically-controlled rotational component along the longitudinal axis of the elongate member.

22. A method of robotically driving an elongate member, the method comprising:
   applying a first torque to rotate the elongate member about a longitudinal axis of the elongate member with a robotically-controlled rotational component positioned a first distance away from an insertion site along the elongate member;
   applying axial motion to the elongate member to axially move the elongate member with respect to the rotationally-controlled rotational component;
   applying a second torque to rotate the elongate member about the same longitudinal axis of the elongate member with a robotically-controlled rotational support positioned a second distance away from the insertion site along the elongate member, and wherein the second distance is longer than the first distance, wherein the second torque is different in magnitude from the first torque; and
   shortening a length of a portion of the elongate member between the robotically-controlled rotational component and the robotically-controlled rotational support to insert the elongate member into the insertion site.

23. A method of robotically driving an elongate member, the method comprising:
   gripping the elongate member with a robotically-controlled component at a first distance away from an insertion site along the elongate member;
   supporting the elongate member with a robotically-controlled support at a second distance away from the insertion site along the elongate member, the second distance being longer than the first distance;

aligning a first portion of the elongate member with an insertion axis, the first portion being between the robotically-controlled component and the robotically-controlled support;

turning a second portion of the elongate member relative to the first portion so that the second portion is not aligned with the insertion axis, the second portion being between the robotically-controlled component and the robotically-controlled support;

shortening a length of the second portion of the elongate member to insert the elongate member into the insertion site; and applying a torque to the elongate member with the robotically-controlled support at the second distance away from the insertion site to rotate the elongate member about a longitudinal axis of the elongate member.

24. The method of claim 23, further comprising applying axial motion to the elongate member with the robotically-controlled component to axially move the elongate member.

* * * * *